(12) United States Patent
Canullo

(10) Patent No.: US 8,690,572 B2
(45) Date of Patent: Apr. 8, 2014

(54) IMPLANT SYSTEM

(75) Inventor: Luigi Canullo, Rome (IT)

(73) Assignee: H&F SRL, Rome (IT)

( * ) Notice: Subject to any disclaimer, the term of this patent is extended or adjusted under 35 U.S.C. 154(b) by 82 days.

(21) Appl. No.: 12/987,384

(22) Filed: Jan. 10, 2011

(65) Prior Publication Data

US 2011/0151407 A1    Jun. 23, 2011

Related U.S. Application Data

(63) Continuation of application No. PCT/IT2009/000300, filed on Jul. 8, 2009.

(30) Foreign Application Priority Data

Jul. 11, 2008  (IT) .............................. RM2008A0376

(51) Int. Cl.
*A61C 8/00*         (2006.01)

(52) U.S. Cl.
USPC ......................................................... 433/174

(58) Field of Classification Search
USPC ...................... 433/172–176, 201.1
See application file for complete search history.

(56) References Cited

U.S. PATENT DOCUMENTS

| | | | | |
|---|---|---|---|---|
| 4,552,532 A * | 11/1985 | Mozsary | ........................ | 433/173 |
| 5,040,982 A * | 8/1991 | Stefan-Dogar | ................ | 433/169 |
| 5,282,746 A | 2/1994 | Sellers et al. | | |
| 5,316,476 A * | 5/1994 | Krauser | ......................... | 433/173 |
| 5,458,488 A * | 10/1995 | Chalifoux | ...................... | 433/173 |
| 5,695,335 A * | 12/1997 | Haas et al. | ..................... | 433/173 |
| 5,695,336 A * | 12/1997 | Lazzara et al. | ................. | 433/173 |
| 5,816,812 A | 10/1998 | Kownacki et al. | | |
| 6,205,837 B1 | 3/2001 | Sapkos | | |
| 6,474,991 B1 | 11/2002 | Hansson | | |
| 7,204,692 B2 * | 4/2007 | Klardie et al. | ................. | 433/173 |
| 7,780,446 B2 * | 8/2010 | Sanchez et al. | ............... | 433/173 |
| 2002/0123022 A1 * | 9/2002 | Pilla et al. | ...................... | 433/173 |
| 2002/0182567 A1 * | 12/2002 | Hurson et al. | ................. | 433/173 |
| 2004/0091837 A1 | 5/2004 | Horiuchi | | |
| 2004/0170947 A1 * | 9/2004 | Milne | ........................... | 433/173 |
| 2006/0141418 A1 * | 6/2006 | Heo | ............................... | 433/173 |
| 2010/0047741 A1 * | 2/2010 | Blaim et al. | .................... | 433/173 |
| 2010/0304334 A1 * | 12/2010 | Layton | ........................... | 433/173 |
| 2011/0151408 A1 * | 6/2011 | Grant | ............................. | 433/174 |
| 2012/0178047 A1 * | 7/2012 | Sanchez et al. | ................ | 433/173 |
| 2012/0231418 A1 * | 9/2012 | Layton | ........................... | 433/173 |

OTHER PUBLICATIONS

International Search Report based on International Application No. PCT/IT2009/000300 with an International Completion Filing Date of Jul. 8, 2009, 3 pages.
International Preliminary Report on Patentability and Written Opinion of the International Searching Authority issued on Jan. 11, 2011 in connection with International Patent Application No. PCT/USIT2009/000300 filed on Jul. 8, 2009, 7 pages.

* cited by examiner

*Primary Examiner* — Hao D Mai
(74) *Attorney, Agent, or Firm* — Gesmer Updegrove LLP

(57) ABSTRACT

An improved implant system including a self-threading screw, preferably comprised of titanium, to be inserted and Osseo-integrated within the patient jaw, and having an inner upper threading, and a pin, preferably formed of titanium, on which pin a dental crown is coupled. The implant system is characterized in that the coupling zone between the self-threading screw and the pin has an abutment platform having an inclination directed upward, from inside toward outside. In the end portion of the platform is provided a space between the pin outer surface and the screw inner surface.

6 Claims, 2 Drawing Sheets

IMPLANT SYSTEM

PRIORITY DATA

The present application is a continuation application of PCT/IT2009/000300 filed on Jul. 8, 2009, which claims priority to Italian Patent Application Serial No. RM2008A000376 filed Jul. 11, 2008, the entire disclosures of which are hereby incorporated by reference.

BACKGROUND

The present invention relates to an improved implant prosthetic system.

More specifically, the invention relates to an implant system of the above kind permitting obtaining optimum bore absorption and an aesthetically pleasant emergency profile.

As it is well known, modern implantology is based on studies carried out by Branemark during the seventies. The solution suggested in the past years by Branemark provided the insertion of a titanium self-tapping screw within the patient bone to be then used as anchorage of a titanium pin. A crown is then cemented or screwed onto the pin.

Coupling between the implant and the pin always involves a bone re-absorption, varying between 2 and 3 mm, and essentially depends on two different factors:
bacterial colonization occurring within the micro-space at the junction between the implant platform and the pin platform, causing a chronic infection of the surrounding bone (restoration of the biological thickness); and
distribution of the occlusion stresses on the bone surface at the level of the implant edge.

It is known that bone re-absorption always causes a gingival defect.

Recently, solutions have been suggested involving employing a bigger implant and coupling it by a standard pin, wherein bone re-absorption is remarkably reduced (this technology is known as platform switching or platform shifting).

It has also been observed that bone re-absorption is directly proportional to the difference between the implant diameter and pin diameter (difference between implant/abutment).

In order to exploit advantages of this technique, the doctor must always use implants having a diameter larger than necessary, thus being difficult to be introduced.

Furthermore, all implants used for this kind of technique have a flat platform or a platform having a flaring or inclination faced upward (in FIG. 1 of the enclosed drawings it is shown at 10 an example of an implant having a platform faced upward, while in FIG. 2 it is shown at 12 a section of an implant with a flat platform), Such solutions, mainly in case a platform switching is employed, always involve the presence of an emergency profile that can be difficulty covered by gingival edge.

SUMMARY

In view of the above, the Applicant has surprisingly found that, starting from the switching platform solution, realizing an inverted platform, i.e. with flaring or inclination faced toward the implant apex, it is possible obtaining an optimum bone re-absorption and an aesthetically pleasant emergency profile.

It is therefore specific object of the present invention an improved implant system, including a self-threading screw, preferably comprised of titanium, to be inserted and Osseo-integrated within the patient jaw, and having an inner upper threading, and a pin, preferably formed of titanium, on which pin a dental crown is coupled. The implant system is characterized in that the coupling zone between the self-threading screw and the pin has an abutment platform having an inclination directed upward, from inside toward outside. In the end portion of the platform is provided a space between the pin outer surface and the screw inner surface.

Preferably, according to the invention, the pin provides a profile diverging outward in correspondence of the coupling with the self-threading screw in order to create a further growth space for gum, and thus a sealing.

Particularly, according to the invention, the abutment platform has an inclination between 20° and 60°, preferably an inclination between 25° and 40°, and particularly an inclination of about 32°.

Still according to the invention, the diameter of connection between the self-threading and pin may be between 3.3 mm and 3.8 mm.

Always according to the invention, the diameter of abutment platform ranges between 4.0 mm and 5.5 mm.

BRIEF DESCRIPTION OF THE DRAWINGS

The present invention will be now described, for illustrative but not limitative purposes, according to its preferred embodiments, with particular reference to the enclosed drawings, wherein.

DETAILED DESCRIPTION

Figure 1:
FIG. 1 is a perspective view of a first implant system according the known art.
Figure 1:
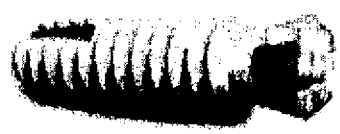
Figure 2:
FIG. 2 is a section view of a second implant system according to the known art.
Figure 2:
Figure 3:
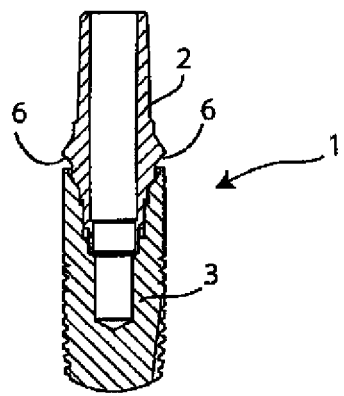
FIG. 3 schematically shows an improved implant system according to the present invention.
Figure 4:
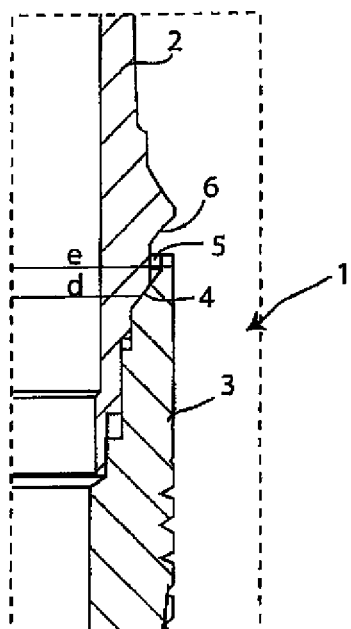
FIG. 4 shows a particular of the implant system of FIG. 3.

Observing now FIGS. 3 and 4 of the enclosed drawings, an implant system according to the invention is shown, generically indicated by reference number 1, having a pin 2 to be inserted within patient jawbone and a self-threading screw 3 to be coupled to said pin 2, and that will support the tooth.

In FIG. 4 it is shown a particular of coupling between pin 2 and self-threading screw 3, providing a coupling platform 4, having an inclination upward. A space 5 is provided between pin 2 and self-threading screw 3, in correspondence of the platform 4, having a walling off function. Furthermore, said pin 2 has a profile 6 diverging outward in correspondence of coupling with self-threading screw 3, in order to create a further space for growing of gingiva, and thus a further walling off space.

Gingiva grows within space 5, 6, thus realising an optimum walling off.

Diameter of platform 4 and connection ray are respectively indicated by references "e" and "d".

As it is well evident from the previous specification, the solution suggested according to the invention has different advantages with respect to the known solutions, and particularly:
displacement downward of the profile emerging from implant, with a consequent aesthetical improvement;
increase of mismatching between implant and pin, due to the fact that the platform is a hypotenuse of a rectangle triangle;
a better load distribution, with a consequent reduced stress on the bone/implant edge, due, as demonstrated by a finite element analyses, to the inclined coupling instead of the flat coupling.

Rounded shape of the pin emergency profile further permits grow of a fibrotic dense tissue that, on the basis of last published researches, also has the walling off function with respect to the bacterial contamination (walling off function). This effect can be particularly observed in FIG. 4.

Double coupling provided further permits a stability of connection, with remarkable structural benefits.

Under a strictly engineering point of view, inclination has an angle between 20° and 60°, with an optimum value of about 45°.

Diameter of connection can be included within the range of 3.8-5.5 mm.

Diameter of implant platform can be included within the range of 4.0-5.5 mm.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. An implant system, comprising:
a self-threading screw, comprised of titanium, configured to be inserted and osseo-integrated within a patient jaw, and having an inner upper threading; and
a pin, comprised of titanium, configured for a dental crown to be coupled thereon;
wherein said self-threading screw and said pin define a coupling zone therebetween when said in is coupled to a proximal end portion of said self-threading screw; said coupling zone comprises an abutment platform, which has an inclination outwardly in a proximal direction with respect to a longitudinal axis of the implant system;
wherein a coronal end portion of said abutment platform being provided an annular space between an outer surface of said pin and an inner surface of said self-threading screw, said annular space being defined, in part, by an outer radial wall portion of the pin and an inner radial wall portion of the screw, wherein the inner and outer radial wall portions are generally parallel with respect to each other and to the longitudinal axis;
wherein coronally of said outer radial wall portion of said pin providing an outward diverging profile, said outward diverging profile extending initially vertically and proximally with respect to the longitudinal axis as an extension of the outer radial wall portion of the pin prior to diverging radially outward in the proximal direction, and said outward diverging profile together with the annular space providing a further space for growing of gum tissues, and thus a sealing space;
wherein said extension of the outer radial wall portion of the pin extends proximally beyond a proximal end of the self-threading screw; and wherein the outward diverging profile is proximally spaced from the proximal end of the self-threading screw.

2. The implant system according to claim 1, wherein the inclination with respect to the longitudinal axis is between 20° and 60°.

3. The implant system according to claim 2, wherein the inclination with respect to the longitudinal axis is between 25° and 40°.

4. The implant system according to claim 3, wherein the inclination with respect to the longitudinal axis is about 32°.

5. The implant system according to claim 1, wherein a diameter of connection between the self-threading screw and the pin is between 3.3 mm and 3.8 mm.

6. The implant system according to claim 1, wherein a diameter of the abutment platform ranges between 4.0 mm and 5.5 mm.

* * * * *